United States Patent
Krämer et al.

[11] Patent Number: 5,990,140
[45] Date of Patent: *Nov. 23, 1999

[54] SUBSTITUTED OXAZOLINES OF THE FORMULA (I)

[75] Inventors: Wolfgang Krämer, Burscheid; Reiner Fischer, Monheim; Graham Holmwood, Wuppertal; Hermann Hagemann, Leverkusen; Ulrike Wachendorff-Neumann, Neuwied; Christoph Erdelen, Leichlingen; Andreas Turberg, Erkrath; Norbert Mencke, Leverkusen, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/669,501

[22] PCT Filed: Jan. 4, 1995

[86] PCT No.: PCT/EP95/00021

§ 371 Date: Jul. 10, 1996

§ 102(e) Date: Jul. 10, 1996

[87] PCT Pub. No.: WO95/19349

PCT Pub. Date: Jul. 20, 1995

[30] Foreign Application Priority Data

Jan. 17, 1994 [DE] Germany ............................ 44 01 099

[51] Int. Cl.⁶ ...................... A01N 43/76; C07D 263/10; C07D 263/12; C07D 263/14

[52] U.S. Cl. ...................... 514/374; 548/237; 548/238; 548/239

[58] Field of Search ............................ 514/374; 548/237, 548/239, 238

[56] References Cited

U.S. PATENT DOCUMENTS

| | | | |
|---|---|---|---|
| 2,372,409 | 3/1945 | Tryon | 548/237 |
| 3,777,031 | 12/1973 | Chen et al. | 514/374 |
| 3,901,906 | 8/1975 | Kozlik | 260/307 F |
| 4,045,447 | 8/1977 | Arlt | 548/237 |
| 4,216,162 | 8/1980 | Arlt | 548/237 |
| 5,807,877 | 9/1998 | Lantzsh et al. | 514/374 |

FOREIGN PATENT DOCUMENTS 0345775  12/1989  European Pat. Off. .

OTHER PUBLICATIONS

English Abstract of JO 2235–874–A, Pharmaceuticals, p.27, Week 9043 (1990).
English Abstract of J 5 7058–641, Pharmaceuticals, p.3, Week E20 (1980).
English translaton of the claims of JO 2235–872–A.
English translation of the claims of J 5 7058–641.
English translation of Japanese Patent 2235872.
Puesen et al. Chem. Abstr. vol. 120 p. 1049, entry 217380e, 1994.
Michelo et al. Chem. Abstr. vol. 118, p. 749 entry 255223f, 1992.
Umezawa et al Chem. Abstr. vol. 116, p. 820 entry 83659j, 1992.
Toshimitsu et al. Chem. Abstr. vol. 114, p. 798 entry 122355n, 1991.
Kurth et al. Chem. Abstr vol. 102, p. 565 entry 45822k, 1985.
Shibata et al. Chem Abstr vol. 98, p. 566 entry 106914, 1983.
Japan Tobacco Chem Abstr vol. 97, p. 581 entry 109704, 1982.
Bates et al Chem. Abstr. vol. 94, p. 432 entry 15626, 1981.
Harder et al. Chem Abstr. vol. 125 entry 317321, 1996.

*Primary Examiner*—Mukund J. Shah
*Assistant Examiner*—Brenda Coleman
*Attorney, Agent, or Firm*—Sprung Kramer Schaefer & Briscoe

[57] ABSTRACT

The invention relates to novel substituted oxazolines of the formula (I)

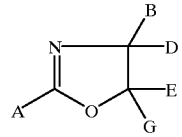

(I)

in which

A, B, D, E and G have the meaning given in the description, to a number of processes for their preparation and to their use as agents for combating pests.

6 Claims, No Drawings

SUBSTITUTED OXAZOLINES OF THE FORMULA (I)

This application is a 371 of PCT/EP95/00021, filed Jan. 4, 1995.

The invention relates to novel substituted oxazolines, to a number of processes for their preparation, and to their use for combating animal pests.

It is already known that certain oxazoline derivatives have insecticidal and acaricidal properties (cf. EP-A 0 345 775 and EP-A 0 432 661). However, the activity of these previously known compounds, especially at low application rates and concentrations, is not completely satisfactory in all areas of application.

The novel substituted oxazolines of the formula (I)

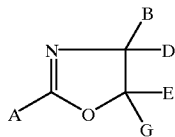
(I)

have now been found, in which

A represents in each case optionally substituted alkyl, alkenyl, cycloalkyl or cycloalkenyl;

B represents in each case optionally substituted phenyl, phenylalkyl, phenylalkenyl, phenoxyalkyl or phenylthioalkyl;

D represents hydrogen or alkyl;

E represents hydrogen or alkyl; and

G represents hydrogen or alkyl.

Depending on the nature of the substituents the compounds of the formula (I) may also be present as geometrical and/or optical isomers or mixtures of isomers of different composition. The invention relates both to the pure isomers and to the isomer mixtures.

Furthermore it has been found that substituted oxazolines of the formula (I) are obtained in that a) amino alcohols of the formula (II)

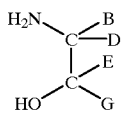
(II)

in which
B, D, E and G have the meanings given above
are reacted with a carboxylic acid of the formula (III)

A—COOH (III)

in which
A has the meaning given above
with a dehydrating agent and, if desired, in the presence of a diluent; or b) amido alcohols of the formula (IV)

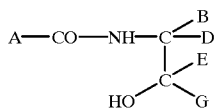
(IV)

in which
A, B, D, E and G have the meanings given above
are reacted with a dehydrating agent, if desired in the presence of a diluent; or c) amide derivatives of the formula (V)

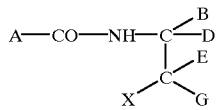
(V)

in which
A, B, D, E and G have the meanings given above; and
X represents a leaving group such as halogen, alkylsulfonyloxy or arylsulfonyloxy,
are reacted with a base, if desired in the presence of a diluent.

Furthermore it has been found that substituted oxazolines of the formula (I) are very highly suited to the combating of animal pests. They are particularly notable for their high level of activity against arthropods and nematodes.

Surprisingly, the substituted oxazolines of the formula (I) according to the invention display a considerably better activity against animal pests than the prior art compounds whose constitution is closest to that of the novel compounds.

A general definition of the compounds according to the invention is given by the formula (I).

A preferably represents $C_1$–$C_8$-alkyl which is optionally substituted one or more times by identical or different substituents chosen from halogen, cyano and $C_1$–$C_4$-alkoxy and from phenyl, phenoxy, benzyloxy, phenylthio and benzylthio, each of which is optionally substituted one to three times by identical or different substituents chosen from halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and/or $C_1$–$C_4$-halogenoalkylthio;

represents $C_2$–$C_8$-alkenyl which is optionally substituted one or more times by identical or different halogen substituents;

represents $C_3$–$C_8$-cycloalkyl which is optionally substituted one or more times by identical or different substituents chosen from halogen, $C_1$–$C_4$-alkyl, $C_2$–$C_4$-alkenyl, $C_1$–$C_4$-halogenoalkyl or $C_2$–$C_4$-halogenoalkenyl;

and represents $C_5$–$C_7$-cycloalkenyl which is optionally substituted one or more times by identical or different substituents chosen from halogen, $C_1$–$C_4$-alkyl and $C_1$–$C_4$-halogenoalkyl.

B preferably represents phenyl, benzyl, pheneth-1-yl, pheneth-2-yl, phenoxymethyl, phenylthiomethyl, phenoxyeth-1-yl, phenylthioeth-1-yl, phenoxyeth-2-yl or styryl, each of which is optionally substituted one to four times by identical or different substituents, phenyl substituents which may be mentioned being in each case halogen, $C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by 1–3 further oxygen atoms,
$C_1$–$C_{18}$-alkylthio,
$C_1$–$C_8$-halogenoalkylthio,
3,4-difluoromethylenedioxo,
3,4-tetrafluoroethylenedioxo,
benzyliminooxymethyl which is optionally substituted by $C_1$–$C_4$-alkyl, $C_3$–$C_6$-cycloalkyl and/or halogen, cyclohexyl and cyclohexyloxy, each of which is optionally substituted by $C_1$–$C_6$-alkyl, $C_1$–$C_6$-alkoxy, cyclohexyl or phenyl;
pyridyloxy which is optionally substituted once or twice by identical or different substituents chosen from halogen, $C_1$–$C_4$-alkyl or $C_1$–$C_4$-halogenoalkyl; phenyl, benzyl, phenoxy, phenylthio, benzyloxy and benzylthio, each of which is optionally substituted one to three times by identical or different substituents chosen from $C_1$–$C_{12}$-alkyl, halogen, $C_1$–$C_4$-halogenoalkyl, $C_1$–$C_6$-alkoxy, $C_1$–$C_6$-halogenoalkoxy, $C_1$–$C_6$-alkoxy-$C_1$–$C_6$-alkyl, $C_1$–$C_6$-alkoxyethyleneoxy, $C_1$–$C_6$-alkylthio and/or $C_1$–$C_6$-halogenoalkylthio.

D preferably represents hydrogen or methyl.
E preferably represents hydrogen or methyl.
G preferably represents hydrogen or methyl.
A particularly preferably
represents $C_1$–$C_6$-alkyl which is optionally substituted one or more times by identical or different substituents chosen from
fluorine, chlorine, bromine, cyano and $C_1$–$C_2$-alkoxy and by phenyl, phenoxy, benzyloxy, phenylthio and benzylthio, each of which is optionally substituted once or twice by identical or different substituents chosen from fluorine, chlorine, $C_1$–$C_4$-alkyl, $C_1$–$C_2$-halogenoalkyl, $C_1$–$C_2$-alkoxy, $C_1$–$C_2$-halogenoalkoxy, $C_1$–$C_2$-alkylthio and/or $C_1$–$C_2$-halogenoalkylthio;
represents $C_2$–$C_6$-alkenyl which is optionally substituted one or more times by identical or different substituents chosen from fluorine, chlorine and/or bromine;
represents $C_3$–$C_8$-cycloalkyl which is optionally substituted one or more times by identical or different substituents chosen from fluorine, chlorine, $C_1$–$C_4$-alkyl and $C_2$–$C_4$-alkenyl, and by $C_1$–$C_2$-alkyl or $C_2$–$C_4$-alkenyl, each of which is substituted by fluorine and/or chlorine,
and represents $C_5$–$C_7$-cycloalkenyl which is optionally substituted one or more times by identical or different substituents chosen from fluorine, chlorine and $C_1$–$C_4$-alkyl and from $C_1$–$C_2$-alkyl which is substituted by fluorine and/or chlorine.

B particularly preferably represents phenyl, benzyl, pheneth-1-yl, pheneth-2-yl, phenoxymethyl, phenylthiomethyl, phenoxyeth-1-yl, phenoxyeth-2-yl, phenylthioeth-1-yl or styryl, each of which is optionally substituted one to four times by identical or different substituents, substituents for phenyl which may be mentioned being in each case
F, Cl, Br,
$C_1$–$C_{18}$-alkyl,
$C_1$–$C_6$-alkoxy-$C_1$–$C_8$-alkyl,
$C_1$–$C_8$-alkoxy which is substituted one to six times by identical or different substituents chosen from F and/or Cl,
$C_1$–$C_2$-alkyl which is substituted one to five times by identical or different substituents chosen from F and/or Cl,
$C_1$–$C_{18}$-alkoxy and —$(OC_2H_4)_{1-3}$—O—$C_1$–$C_6$-alkyl,
$C_1$–$C_{12}$-alkylthio,
$C_1$–$C_8$-alkylthio which is substituted one to six times by identical or different substituents chosen from F and/or Cl,
3,4-difluoromethylenedioxo,
3,4-tetrafluoroethylenedioxo,
the groups cyclohexyl and cyclohexyloxy, each of which is optionally substituted by $C_1$–$C_4$-alkyl, $C_1$–$C_4$-alkoxy, cyclohexyl or phenyl; pyridyloxy which is optionally substituted once or twice by identical or different substituents chosen from F, Cl or $CF_3$;
phenyl, benzyl, phenoxy, phenylthio, benzyloxy and benzylthio, each of which is optionally substituted one to three times by identical or different substituents chosen from $C_1$–$C_{12}$-alkyl, F, Cl, Br, $CF_3$ and $C_1$–$C_4$-alkoxy, $C_1$–$C_4$-alkoxy which is substituted one to six times by identical or different substituents chosen from F and/or Cl, $C_1$–$C_4$-alkoxy-$C_1$–$C_4$-alkyl, $C_1$–$C_4$-alkoxyethyleneoxy, $C_1$–$C_4$-alkylthio, or $C_1$–$C_4$-alkylthio which is substituted one to six times by identical or different substituents chosen from F and/or Cl.

D particularly preferably represents hydrogen or methyl.
E particularly preferably represents hydrogen or methyl.
G particularly preferably represents hydrogen or methyl.
Preferred compounds according to the invention are also groups of substances of the formulae (I-1) to (I-10):

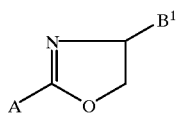
(I-1)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

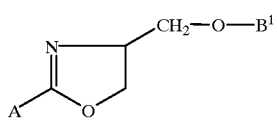
(I-2)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

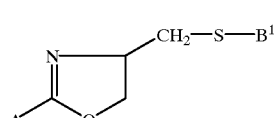
(I-3)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

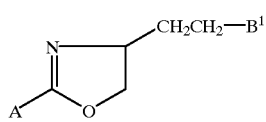
(I-4)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

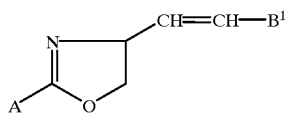
(I-5)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred;

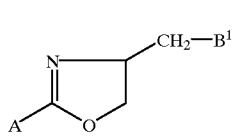
(I-6)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

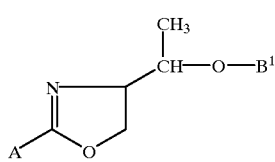
(I-7)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

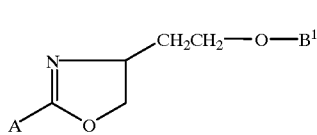
(I-8)

in which

A has the abovementioned general, preferred and particularly preferred meanings, and $B^1$ represents phenyl which is optionally substituted one to four times by identical or different substituents, suitable substituents being the substituents for phenyl mentioned above under (B) as being preferred and particularly preferred.

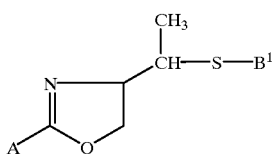
(I-9)

in which

A has the abovementioned general, preferred and particularly preferred meanings, and B¹ represents phenyl which is optionally substituted one to four times by identical or different substituents, suitable substituents being the substituents for phenyl mentioned above under (B) as being preferred and particularly preferred.

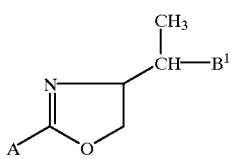
(I-10)

in which

A has the abovementioned general, preferred and particularly preferred meanings, and B¹ represents phenyl which is optionally substituted one to four times by identical or different substituents, suitable substituents being the substituents for phenyl mentioned above under (B) as being preferred and particularly preferred.

Other preferred compounds according to the invention are groups of substances of the formulae (I-1) to (I-10) in which A represents tert-butyl which is optionally substituted one to three times by identical or different substituents, suitable substituents being the substituents for alkyl mentioned above under (A) as being preferred and particularly preferred.

Likewise preferred compounds according to the invention are groups of substances of the formulae (I-1) to (I-10) in which A represents cyclopropyl which is optionally substituted one to five times by identical or different substituents, suitable substituents being the substituents for cycloalkyl mentioned above under (A) as being preferred and particularly preferred.

Additionally preferred compounds according to the invention are groups of substances of the formulae (I-1) to (I-10) in which A represents vinyl which is substituted one to three times by identical or different substituents chosen from fluorine and/or chlorine.

Compounds according to the invention which are also preferred are groups of substances of the formulae (I-11) to (I-20):

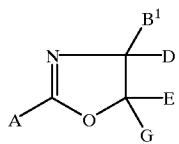
(I-11)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

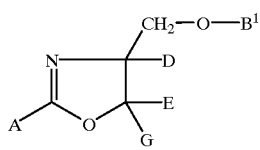
(I-12)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

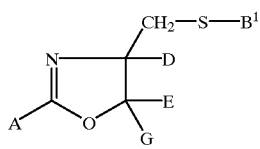
(I-13)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

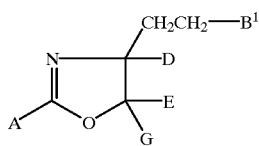

(I-14)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

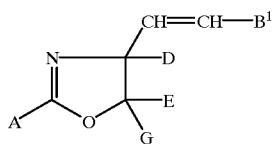

(I-15)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

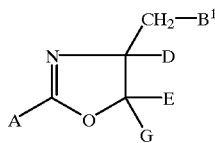

(I-16)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

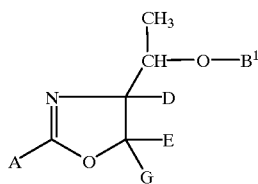

(I-17)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

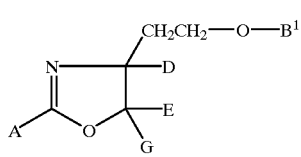

(I-18)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

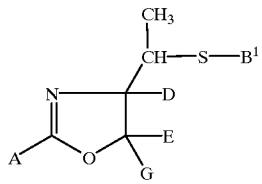

(I-19)

in which

A has the abovementioned general, preferred and particularly preferred meanings;

B¹ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

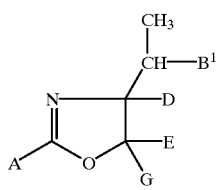

(I-20)

in which

A has the abovementioned general, preferred and particularly preferred meanings;

$B^1$ represents phenyl which is optionally substituted one to four times by identical or different substituents, suitable substituents being the substituents for phenyl mentioned above under (B) as being preferred and particularly preferred; and D, E and G are identical or different and represent hydrogen or methyl, but at least one substituent represents methyl.

Other preferred compounds according to the invention are groups of substances of the formulae (I-11) to (I-20) in which A represents tert-butyl which is optionally substituted one to three times by identical or different substituents, suitable substituents being the substituents for alkyl mentioned above under (A) as being preferred and particularly preferred.

Likewise preferred compounds according to the invention are groups of substances of the formulae (I-11) to (I-20) in which A represents cyclopropyl which is optionally substituted one to five times by identical or different substituents, suitable substituents being the substituents for cycloalkyl mentioned above under (A) as being preferred and particularly preferred.

Additionally preferred compounds according to the invention are groups of substances of the formulae (I-11) to (I-20) in which A represents vinyl which is substituted one to three times by identical or different substituents chosen from fluorine and/or chlorine.

The hydrocarbon radicals mentioned above in the definition of the compounds according to the invention, such as alkyl, are, where possible, in each case straight-chain or branched, even in conjunction with heteroatoms, such as in alkoxy.

Examples of substituents A are the following radicals:

| A | A |
|---|---|
| ClCH$_2$—C(CH$_3$)$_2$— | (CH$_2$Cl)$_3$C— |
| FCH$_2$—C(CH$_3$)$_2$— | CH$_3$—C(CH$_2$OCH$_3$)$_2$— |
| CH$_3$—C(CH$_2$Cl)$_2$— | NC—CH$_2$CH$_2$—C(CH$_3$)$_2$ |
| CH$_3$—C(CH$_2$F)$_2$— | CH$_3$—C(C$_2$H$_5$)(CH$_2$OCH$_3$)— |
| Cl$_2$C=CCl— | F$_2$CH=CFCl— |
| Cl$_2$C=CF— | |

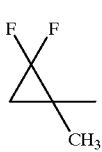

Examples of substituents B are the following radicals:

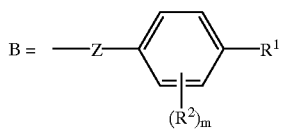

where

Z = a direct bond, —CH$_2$—, —CH(CH$_3$)—, —CH$_2$CH$_2$—, —CH=CH—, —CH$_2$O—, —CH$_2$S—, —CH(CH$_3$)S—, —CH(CH$_3$)O— or —CH$_2$CH$_2$O—, $R^1$ = in accordance with Table 1 and $(R^2)_m$ = in accordance with Table 2.

TABLE 1

| $R^1$ | $R^1$ | $R^1$ |
|---|---|---|
| Cl | —OCF$_2$CHFCF$_3$ | —C$_{10}$H$_{21}$-n |
| F | —CH$_2$CH$_2$—O—C$_2$H$_5$ | —C$_8$H$_{17}$-n |
| —C$_4$H$_9$-t | —CH$_2$CH$_2$—O—C$_4$H$_9$-n | —C$_9$H$_{19}$-n |
| —C$_6$H$_{13}$-n | —CH$_2$CH$_2$—O—C$_6$H$_{13}$-n | CF$_3$ |
| —C$_{12}$H$_{25}$-n | —SCF$_2$CHFCH$_3$ | —SCF$_2$CHF$_2$ |
| —CF$_2$CHF$_2$ | —SC$_4$H$_9$-n | —OCF$_3$ |
| —OC$_6$H$_{13}$-n | —SC$_6$H$_{13}$-n | —OCF$_2$CHF$_2$ |
| —OC$_8$H$_{17}$-n | —SC$_8$H$_{17}$-n | —OCH$_2$CF$_3$ |
| —OC$_{12}$H$_{25}$-n | —SC$_{12}$H$_{25}$-n | —OCF$_2$CHFCH$_3$ |

TABLE 1-continued
| R¹ | R¹ | R¹ |
|---|---|---|
| —SCF₃ | 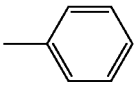 |  |
| 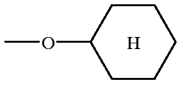 | 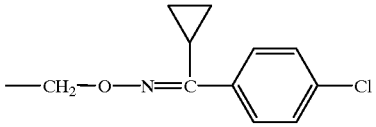 | 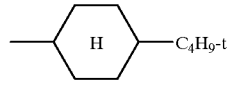 |
|  |  | 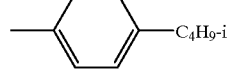 |
|  | 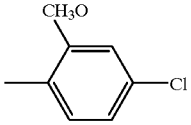 | 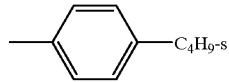 |
| 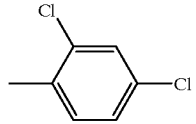 | 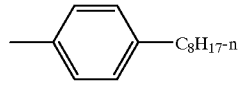 | 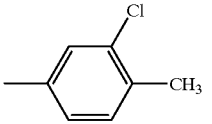 |
| 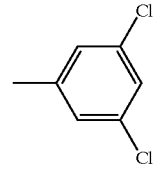 | 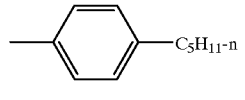 | 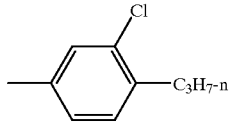 |
| 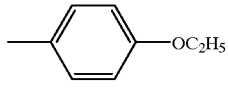 | 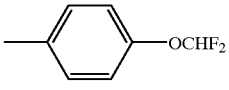 | 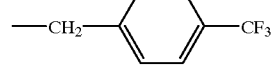 |
| 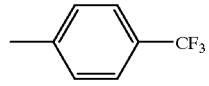 | 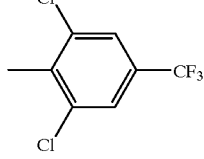 | 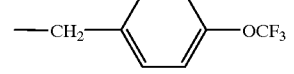 |
| 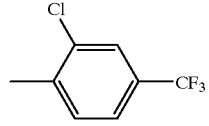 | 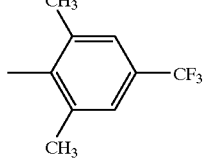 | 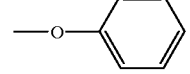 |
| 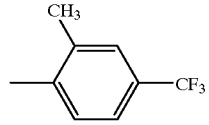 | 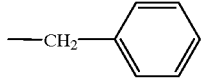 | 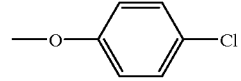 |

TABLE 1-continued
| $R^1$ | $R^1$ | $R^1$ |
|---|---|---|
| 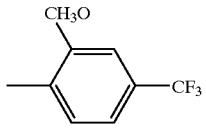 | 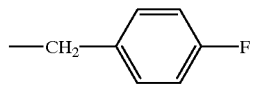 | 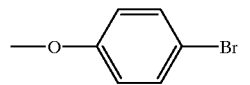 |
| 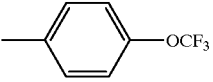 | 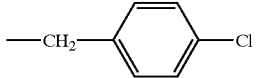 | 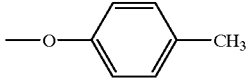 |
| 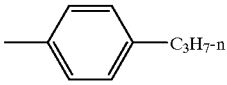 | 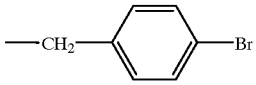 |  |
| 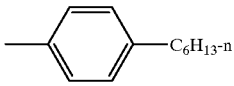 | 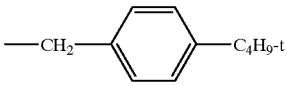 |  |
| 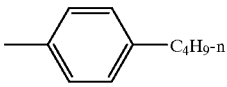 | 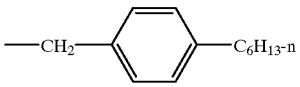 | 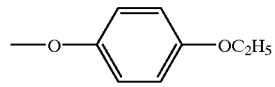 |
| 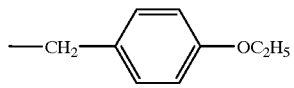 | 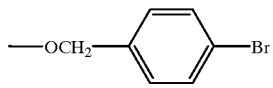 | 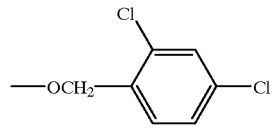 |
|  | 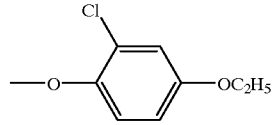 | 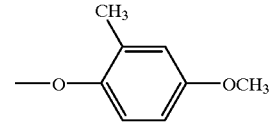 |
| 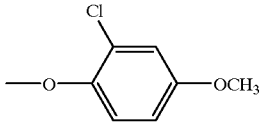 | 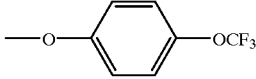 | 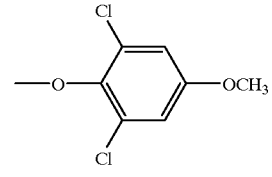 |
| 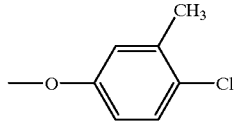 | 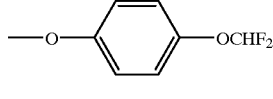 | 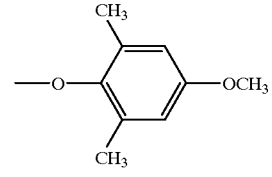 |
|  | 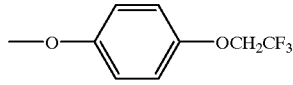 | 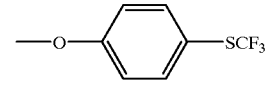 |
| 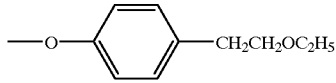 | 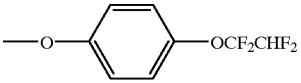 |  |

TABLE 1-continued
| R¹ | R¹ | R¹ |
|---|---|---|
| 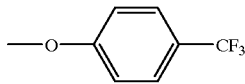 | 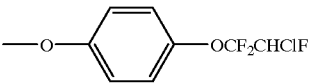 | 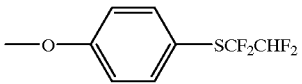 |
| 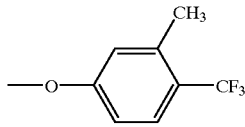 | 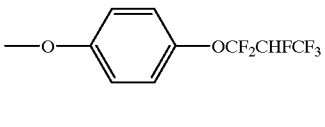 | 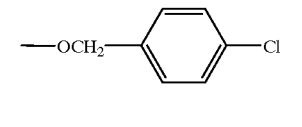 |
| 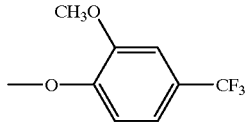 | 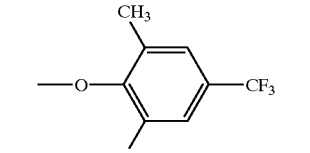 | 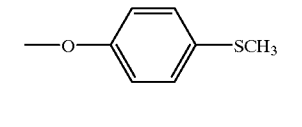 |
| 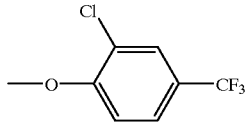 | 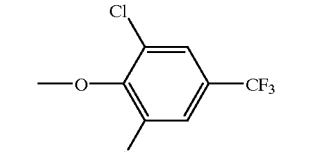 | 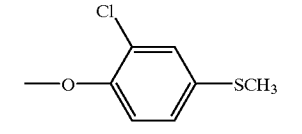 |
| 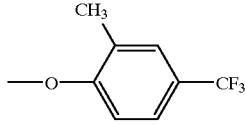 | 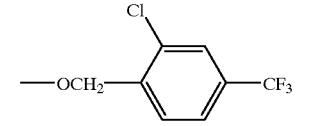 | 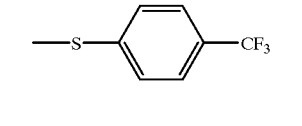 |
| 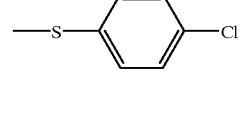 | 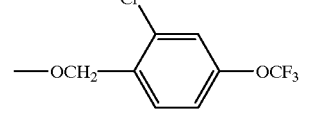 | 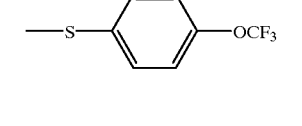 |
| 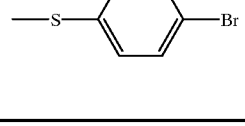 | 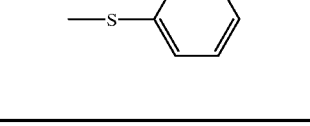 | 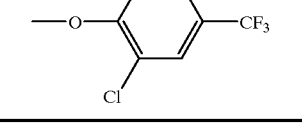 |
TABLE 2
| $(R^2)_m$ | $(R^2)_m$ |
|---|---|
| H | 2-CH$_3$ |
| 2-Cl | 2-OCH$_3$ |
| 2-F | 2-OC$_2$H$_5$ |
| 3-Cl | 3-CH$_3$ |
| 2,6-Cl$_2$ | 3,5-(CH$_3$)$_2$ |
| 3,5-Cl$_2$ | 3-OC$_6$H$_5$ |
| 3,5-F$_2$ | |
| 2,5-Cl$_2$ | together with R¹ represents |
| 3,5-Cl$_2$;2-F | |
| 2,3-F$_2$ | 3,4-OCF$_2$O— and |
| 2,5-F$_2$ | 3,4-OCF$_2$CF$_2$O— |
Individual examples of the compounds of the formula (I) according to the invention are the following:

(I)
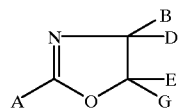
| A | B | D | E | G |
|---|---|---|---|---|
| ClCH$_2$—CFCl— | 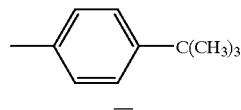 | H | H | H |
| 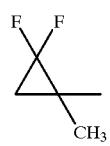 | 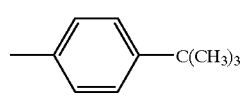 | H | H | H |
|  | 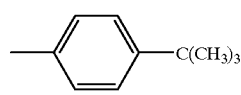 | H | H | H |
| 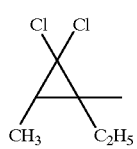 | 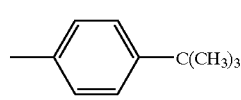 | H | H | H |
| 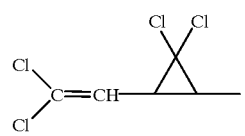 | 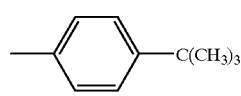 | H | H | H |
| 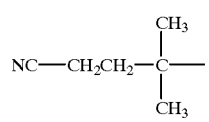 | 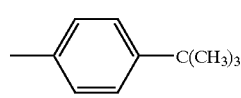 | H | H | H |
| 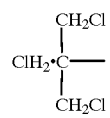 | 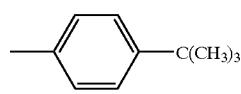 | H | H | H |
| 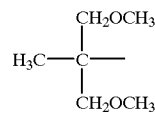 | 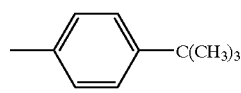 | H | H | H |
| 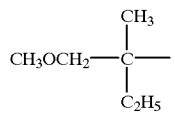 | 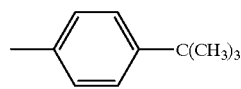 | H | H | H |
| 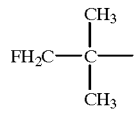 | 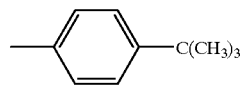 | H | H | H |

-continued
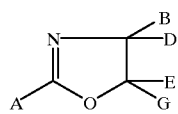
(I)
| A | B | D | E | G |
|---|---|---|---|---|
| 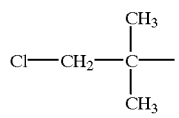 | 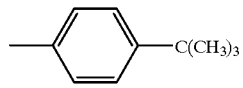 | H | H | H |
| 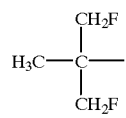 | 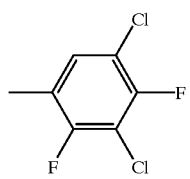 | H | H | H |
| 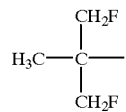 | 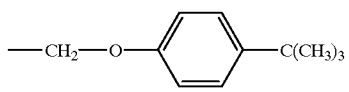 | H | H | H |
| 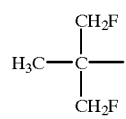 | 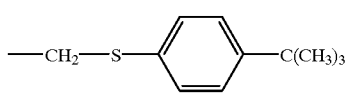 | H | H | H |
| 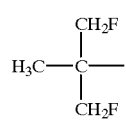 | 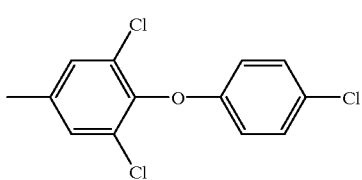 | H | H | H |
| 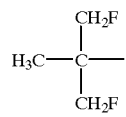 | 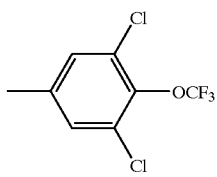 | H | H | H |
| 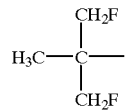 | 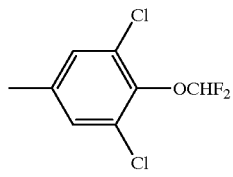 | H | H | H |
| 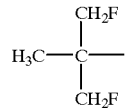 | 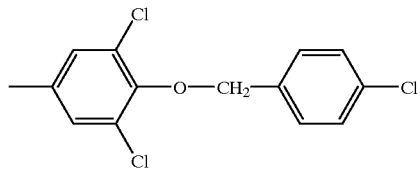 | H | H | H |

-continued
$$\text{(I)}$$
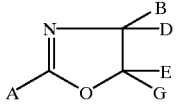
| A | B | D | E | G |
|---|---|---|---|---|
| 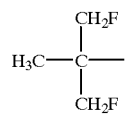 | 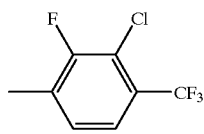 | H | H | H |
| 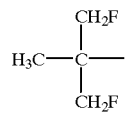 | 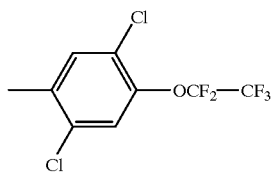 | H | H | H |
| 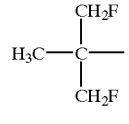 | 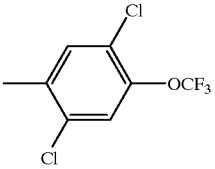 | H | H | H |
| 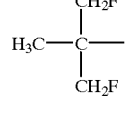 | 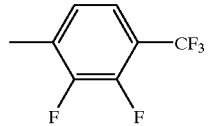 | H | H | H |
| 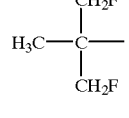 | 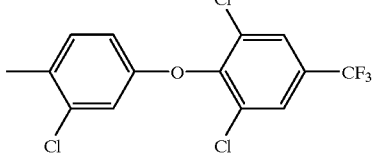 | H | H | H |
| 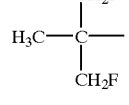 | 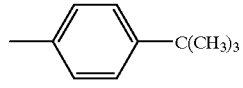 | $CH_3$ | H | H |
| 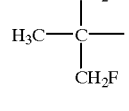 | 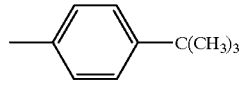 | H | $CH_3$ | $CH_3$ |
| 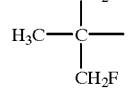 | 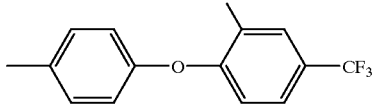 | H | H | H |
| 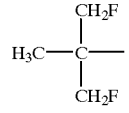 | 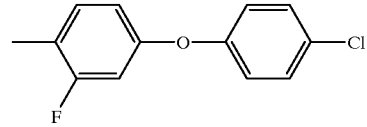 | H | H | H |

-continued
(I)
| A | B | D | E | G |
|---|---|---|---|---|
| 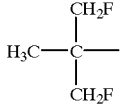 | 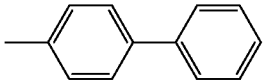 | H | H | H |
| 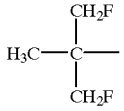 | 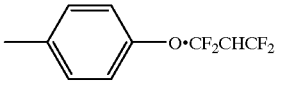 | H | H | H |
| 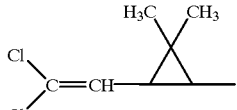 | 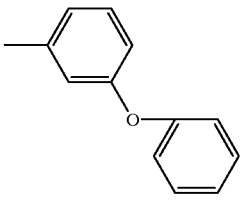 | H | H | H |
| 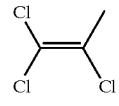 | 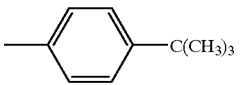 | H | H | H |
| 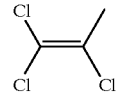 | 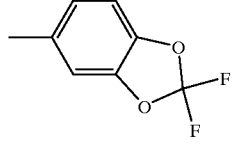 | H | H | H |
| 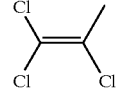 | 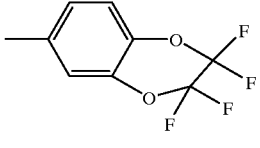 | H | H | H |
| 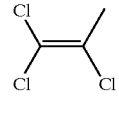 | 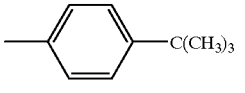 | H | H | H |
| 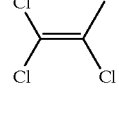 | 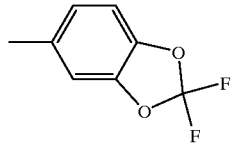 | H | H | H |
| 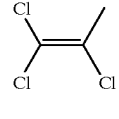 | 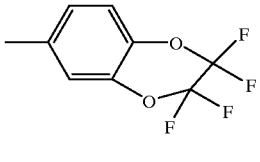 | H | H | H |

-continued

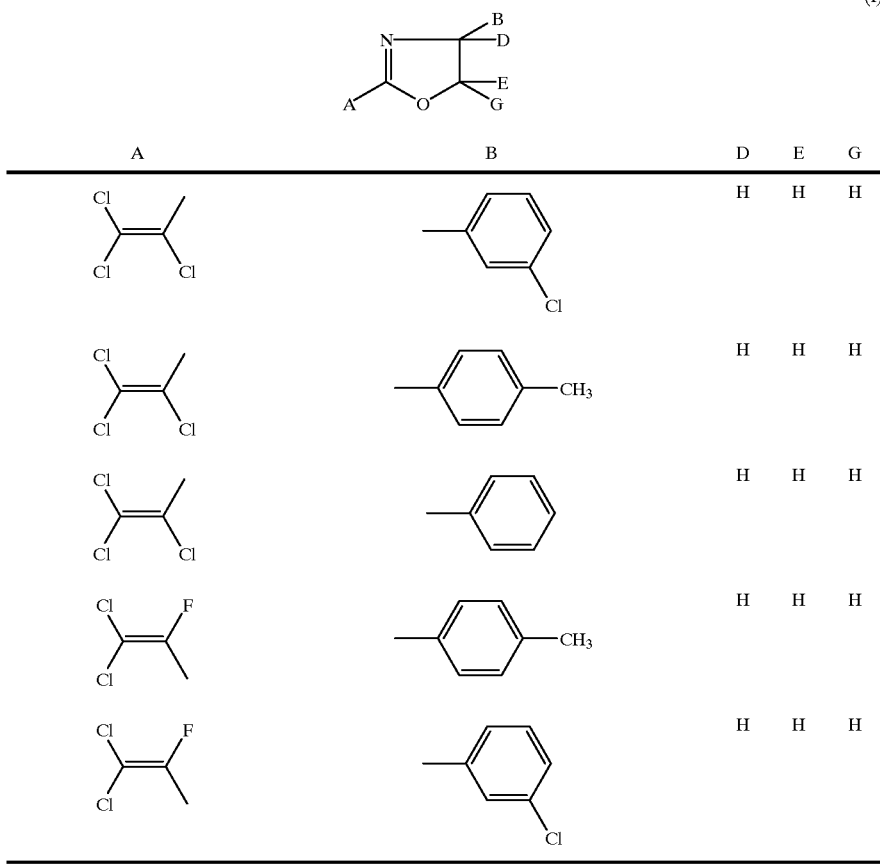

If process (a) according to the invention is carried out using, for example, 2-amino-2-(4-t-butylphenyl)-1-ethanol and 2,2-bis(chloromethyl)-propionic acid as starting materials and polyphosphoric acid (PPS) as dehydrating agent, then the course of the reaction can be indicated by the following equation:

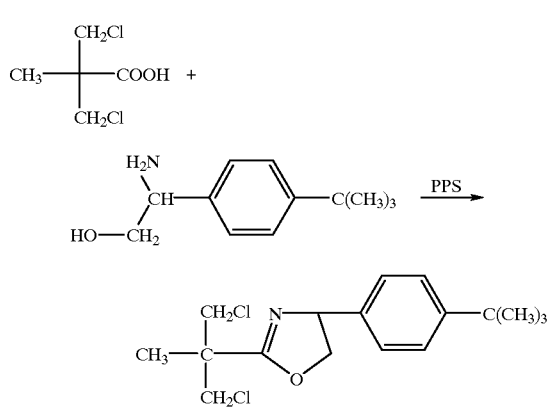

If process (b) according to the invention is carried out using, for example, N-[2-hydroxy-1-(4-t-butylphenyl)-ethyl]-2,2-bis(chloromethyl)-propionamide as starting compound and polyphosphoric acid (PPS) as dehydrating agent, then the course of the reaction can be indicated by the following equation:

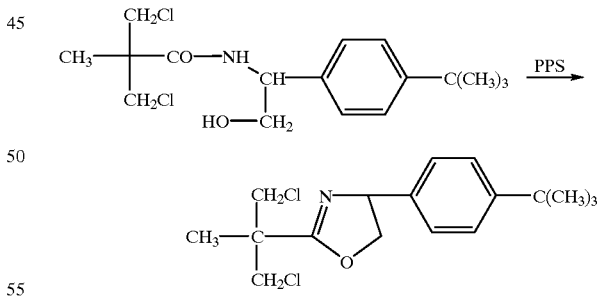

If process (c) according to the invention is carried out using, for example, N-[2-chloro-1-(4-t-butylphenyl)-ethyl]-2,2-bis(chloromethyl)-propionamide as starting compound and triethylamine as base, then the course of the reaction can be indicated by the following equation:

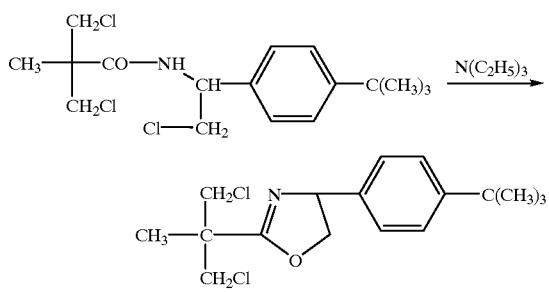

A general definition of the amino alcohols to be used as starting materials in process (a) according to the invention for the preparation of the compounds of the formula (I) is given by the formula (II). In the formula (II) B, D, E and G preferably or in particular have those meanings which have already been given above, in connection with a description of the compounds of the formula (I), as being preferred or, respectively, as being particularly preferred for B, D, E and G.

The starting materials of the formula (II) are known and/or can be prepared by processes which are known per se, by reducing the corresponding amino acids (cf. Heterocycles 9 (1978), 1277–1285; J. Org. Chem. 43 (1978), 2539–2541; Liebigs Ann. Chem. 1980, 122–139; Tetrahedron Lett. 26 (1985), 4971–4974).

A general definition of the carboxylic acids also to be used as starting materials in process (a) according to the invention for the preparation of the compounds of the formula (I) is given by the formula (III). In the formula (III) A preferably or in particular has that meaning which was already given above, in connection with the description of the compounds of the formula (I), as being preferred or, respectively, as being particularly preferred for A.

The starting materials of the formula (III) are known organic synthesis chemicals, and/or are obtainable in a manner known per se.

Processes (a) and (b) according to the invention are carried out using a dehydrating agent. The dehydrating agents which are conventional in organic chemistry can be employed. Preferred possibilities for use are sulfuric acid, polyphosphoric acid (PPS), phosphorus(V) oxide, dicyclohexylcarbodiimide (DCC), phosphorus (V) sulfide and the system triphenylphosphine/triethylamine/tetrachloromethane.

Diluents which are suitable for carrying out processes (a) to (c) according to the invention are the conventional organic solvents. Preferred possibilities in use are aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl or diethyl ether; ketones such as acetone, butanone or methyl isobutyl ketone; nitriles such as acetonitrile, propionitrile or benzonitrile; amides such as N,N-dimethylformamide and N,N-dimethylacetamide, N-methyl-pyrrolidone or hexamethylphosphoric triamide; esters such as methyl acetate or ethyl acetate, and sulfoxides such as dimethyl sulfoxide, and if desired also alcohols such as methanol or ethanol.

When carrying out process (a) according to the invention the reaction temperatures can be varied within a relatively wide range. It is generally carried out at temperatures of between 0° C. and 150° C. preferably at temperatures of between 10° C. and 100° C.

Process (a) according to the invention is generally carried out under atmospheric pressure. However, it is also possible to work under elevated or reduced pressure, generally at between 0.1 bar and 10 bar.

To carry out process (a) according to the invention the particular starting materials required are generally employed in approximately equimolar quantities. However, it is also possible for one of the two components employed in each case to be used in a relatively large excess. The reactions are in general carried out in a suitable diluent in the presence of a dehydrating agent, and the reaction mixture is stirred at the particular temperature required for several hours. The reaction mixture is worked up by conventional methods.

In a particular embodiment of process (a) according to the invention it is possible to use, instead of the carboxylic acids of the formula (III), corresponding nitriles, in which case, preferably, a catalyst such as zinc(II) chloride is used instead of a dehydrating agent.

A general definition of the amido alcohols to be used as starting materials in process (b) according to the invention for the preparation of the compounds of the formula (I) is given by the formula (IV). In the formula (IV) A, B, D, E and G preferably or in particular have those meanings which have already been given above, in connection with the description of the compounds of the formula (I), as being preferred or, respectively, as being particularly preferred for A, B, D, E and G.

The starting materials of the formula (IV) are known and/or can be prepared by methods which are known per se.

The amido alcohols of the formula (IV) are obtained, for example, by reacting acid chlorides derived from the carboxylic acids of the formula (III) with amino alcohols of the formula (II) in the presence of an acid-binding agent such as, for example, triethylamine, pyridine, potassium carbonate, sodium hydroxide or potassium t-butylate, and in the presence of a diluent such as, for example, toluene, chlorobenzene, acetone or acetonitrile, at temperatures of between 0° C. and 100° C. (cf. the preparation examples).

The acid chlorides derived from the carboxylic acids of the formula (III) are largely known and/or can be prepared by methods which are known per se, for example by reacting the carboxylic acids of the formula (III) with a halogenating agent such as thionyl chloride, if desired in the presence of a diluent.

A compound which is as yet unknown, and is likewise the subject of the present invention, is the α-fluoro-β,β-dichloro-acryloyl chloride of the formula (VI)

The α-fluoro-β-β-dichloro-acryloyl chloride of the formula (VI) is obtained by hydrolyzing 2-fluoro-1,1,3,3,3-pentachloropropene, if desired in the presence of a catalyst. Suitable catalysts include Lewis acids, inorganic acids and their acid salts, such as for example $FeCl_3$, $BF_3$, $H_2SO_4$, HCl, $KHSO_4$, $NaHSO_4$, etc. (cf. also the preparation examples).

Depending on the reaction conditions (such as, for example, the residence time of the acid chloride in the reaction mixture) and on the quantity of water added, the α-fluoro-β,β-dichloroacryloyl chloride formed as primary product may if appropriate be particularly hydrolyzed to the corresponding acrylic acid, which can subsequently be converted back to the acid chloride, for example by reaction with thionyl chloride.

When carrying out process (b) according to the invention the reaction temperatures can be varied within a relatively wide range. It is generally carried out at temperatures of between −20° C. and +150° C., preferably at temperatures of between 0° C. and 100° C.

Process (b) according to the invention is generally carried out under atmospheric pressure. However it is also possible to work under elevated or reduced pressure, in general at between 0.1 bar and 10 bar.

To carry out process (b) according to the invention for the preparation of the compounds of the formula (I) requires the use, per mol of amido alcohol of the formula (IV), of in general from 1 to 20 mol, preferably from 1 to 5 mol, of dehydrating agent.

In a preferred embodiment of process (b) according to the invention the amido alcohol of formula (IV) is initially introduced in a diluent, and the dehydrating agent is then metered in. The reaction mixture is stirred at the required temperature until the end of the reaction and is then worked up in a conventional manner.

A general definition of the amide derivatives to be used as starting materials in process (c) according to the invention for the preparation of the compounds of the formula (I) is given by the formula (V). In the formula (V) A, B, D, E and G preferably or in particular have those meanings which have already been given above, in connection with the description of the compounds of the formula (I), as being preferred or, respectively, as being particularly preferred for A, B, D, E and G; X preferably represents fluorine, chlorine, bromine, iodine, $C_1$–$C_4$-alkyl-sulfonyloxy, phenylsulfonyloxy or tolylsulfonyloxy, and in particular represents chlorine, bromine, methylsulfonyloxy or tolylsulfonyloxy.

The starting materials of the formula (V) are known and/or can be prepared by methods which are known per se.

The amide derivatives of the formula (V) are obtained by reacting corresponding amido alcohols of the formula (IV) with chlorinating agents such as, for example, thionyl chloride or phosphorus (V) chloride, or with sulfonylating agents such as, for example, methanesulfonyl chloride or toluenesulfonyl chloride, in a conventional manner, if desired in the presence of a base and if desired in the presence of a diluent.

Process (c) according to the invention is carried out in the presence of a base. In this context all conventional inorganic or organic bases are suitable. Preferred possibilities for use are alkaline earth metal or alkali metal hydrides, hydroxides, amides, alcoholates, acetates, carbonates or hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate and also tertiary amines such as trimethylamine, triethylamine, tributylamine, N,N-di-methylaniline, pyridine, N-methylpiperidine, N,N-dimethylaminopyridine, diazobicyclooctane (DABCO), diazabicyclononene (DBN) or diazabicycloundecene (DBU).

When carrying out process (c) according to the invention the reaction temperatures can be varied within a relatively wide range. It is in general carried out at temperatures of between −20° C. and +150° C. preferably at temperatures of between 0° C. and 100° C.

Process (c) according to the invention is generally carried out under atmospheric pressure. However, it is also possible to work under elevated or reduced pressure, in general at between 0.1 bar and 10 bar.

To carry out process (c) according to the invention for the preparation of the compounds of the formula (I) requires the use, per mol of amide derivative of the formula (V), of in general from 1 to 3 mol, preferably from 1.0 to 1.5 mol, of a base.

In a preferred embodiment of process (c) according to the invention the amide derivative of the formula (V) and a base are mixed in a suitable diluent; the mixture is stirred at the required temperature until the end of the reaction and is then worked up in a conventional manner.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and Tortrix viridana.

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

At appropriate application rates the compounds according to the invention also display a fungicidal action.

The active compounds can be converted to the customary formulations, such as solutions, emulsions, wettable powders, suspensions, powders, dusts, pastes, soluble powders, granules, suspension/emulsion concentrates, natural and synthetic materials impregnated with active compound, very fine capsules in polymeric substances and in coating compositions for seed, and also formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example ligninsulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. The formulations in general contain between 0.1 and 95 percent by weight of active compound, preferably between 0.5 and 90%.

The active compounds according to the invention can be present in their commercially available formulations and in the use forms, prepared from the formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by micro-organisms, inter alia.

The following compounds may be mentioned:
acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-Cyhalothrin, permethrin, pyresmethrin, pyrethrum, silafluofen, tralomethrin, zetamethrin,
alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC xylylcarb, acephate, azinphos A, azinphos M, bromophos A, cadusafos, carbophenothion, chlorfenvinphos, chlormephos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxanthion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclophos, pyridaphenthion, quinalphos, salithion, sebufos, sulfotep, sulprofos, tetrachlorovinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-Chloro-3-pyridinyl)methyl]-N'-cyano-N-methyl-ethaneimideamide (NI-25), abamectin, amitrazin, avermectin, azadirachtin, bensultap, bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice, fleas and worms which live as endoparasites. For example, they display an outstanding activity against ticks such as, for example, *Boophilus microplus*.

The active compounds of the formula (I) according to the invention are also suitable for combating arthropods which infest productive livestock in farming, for example cattle, sheep, goats, horses, pigs, donkeys, camels, buffalo, rabbits, chickens, turkeys, ducks, geese, bees, other domestic animals such as dogs, cats, cage birds, aquarium fish and so-called experimental animals such as, for example, hamsters, guinea-pigs, rats and mice. The intention is, by combating these arthropods, to reduce fatalities and losses in yield (of meat, milk, wool, skins, eggs, honey, etc.), so that the use of the active compounds according to the invention enables the keeping of animals to be more economic and more simple.

The administration of the active compounds according to the invention in the veterinary sector is effected in a known manner by enteral administration in the form of, for example, tablets, capsules, potions, drenches, granules, pastes, boli, by the feed-through method, suppositories, or by parenteral administration, for example by injection (intramuscular, subcutaneous, intravenous, intraperitoneal, etc.), implants, by nasal administration, by dermal administration in the form, for example, of dipping or bathing, spraying, pouring-on and spotting-on, washing, dusting, and using shaped articles containing active compounds, such as collars, eartags, tail tags, limb bands, halters, marking devices, etc.

The preparation and the use of the substances according to the invention are illustrated by the following examples.

PREPARATION EXAMPLES

Example 1

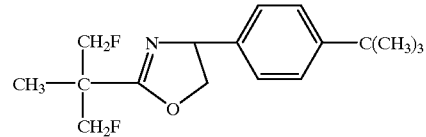

(Process c)

1.6 ml (0.026 mol) of 45% strength sodium hydroxide in 5 ml of water are added dropwise to 4.3 g (0.013 mol) of N-[2-Chloro-1-(4-t-butylphenyl)-ethyl]-2,2-bis (fluoromethyl)-propionamide in 100 ml of methanol under reflux. The reaction mixture is stirred under reflux for 1 hour and then concentrated by distilling off the solvent. The residue is stirred with water and the precipitate is filtered off with suction and dried.

3.8 g (99% of theory) of 2-(1,3-difluoro-2-methyl-prop-2-yl)-4-(4-t-butylphenyl)-1,3-oxazoline are obtained of melting point 62–63° C.

Preparation of the Starting Compound

Example (IV-1)

(Step 1)

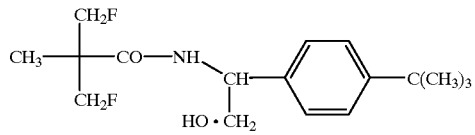

3.3 ml (0.024 mol) of triethylamine are added to 3.9 g (0.02 mol) of 2-amino-2-(4-t-butylphenyl)-1-ethanol in 150 ml of ethyl acetate, and then 3.7 g (0.024 mol) of 2,2-bis (fluoromethyl)-propionyl chloride are added dropwise at 0°

C. The mixture is then allowed to warm to room temperature and is stirred overnight. The precipitate is subsequently filtered off with suction, the filtrate is washed several times with water, and the organic phase is separated off, dried over sodium sulfate, filtered and concentrated.

4.5 g (71.9% of theory) of N-[2-hydroxy-1-(4-t-butylphenyl)-ethyl]-2,2-bis(fluoromethyl)-propionamide are obtained at melting point 141° C.

Example (V-1)

(Step 2)

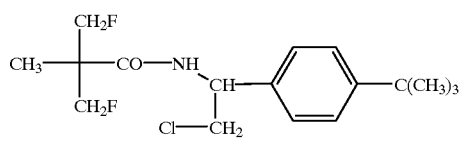

1.05 ml (0.0144 mol) of thionyl chloride are added to 4.5 g (0.0144 mol) of N-[2-hydroxy-1-(4-t-butylphenyl)-ethyl]-2,2-bis (fluoromethyl)-propionamide (cf. step 1) in 100 ml of carbon tetrafluoride. The reaction mixture is allowed to react under reflux for 1 hour. After distilling off the solvent, 4.3 g (90% of theory) of N-[2-Chloro-1-(4-t-butylphenyl)-ethyl]-2,2-bis(fluoromethyl)-propionamide are obtained of melting point 98° C.

Example 2

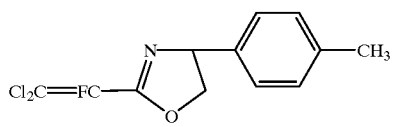

(Process c)

2.8 ml of triethylamine are added to 3.4 g (20 mmol) of 2-(4-methylphenyl)-2-aminoethanol in 50 ml of absolute tetrahydrofuran, and 3.6 g (20 mmol) of 3,3-dichloro-2-fluoro-acryloyl chloride are added dropwise at 0–10° C. After stirring for one hour at room temperature the precipitate is filtered off with suction, the filtrate is concentrated, the residue is taken up in 50 ml of absolute toluene, 4.8 g of thionyl chloride are added, and the mixture is heated under reflux for two hours. The toluene and excess thionyl chloride are removed in vacuuo. The residue is again taken up in toluene, 3 g (22 mmol) of potassium tert-butylate are added in portions, and the mixture is heated at 50° C. while monitoring it by thin-layer chromatography. The reaction mixture is washed with water and the toluene phase is concentrated. The residue is chromatographed on silica gel with 10:1 n-hexane/ethyl acetate.

2.3 g (41% of theory) of 2-(2,2-dichloro-1-fluorovinyl)-4-(4-methylphenyl)-1,3-oxazoline are obtained; $^1$HNMR (500 MHz, CDCl$_3$): 2.33 (s, 3H); 4.25 (t, 1H); 7.15 (m, 4H).

Preparation of the Starting Compounds 515 g of 2-fluoro-1,1,3,3,3-pentachloropropane and 27 g of iron(III) chloride are introduced as initial charge, and 52.6 g of water are added dropwise at 110° C. over the course of 2 hours. The reaction mixture is stirred at 110° C. for 1 hour and cooled to about 70° C., the solids are separated off by filtration, and 330.2 ml of thionyl chloride are added dropwise. After reflux for about 2 hours the excess thionyl chloride and the dichlorofluoroacryloyl chloride are separated off by distillation.

233 g (90% of theory) of dichlorofluoroacryloyl chloride are obtained of boiling point 134° C.

In a corresponding way, and in accordance with the general information for preparation, the following substituted oxazolines of the formula (I) are obtained:

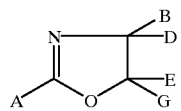

(I)

| Ex. No. | A | B | D | E | G | Physical constant |
|---|---|---|---|---|---|---|
| 3 | CH$_3$—C(CH$_2$Cl)$_2$— | —C$_6$H$_4$—C(CH$_3$)$_3$ | H | H | H | m.p. 86–88° C. |
| 4 | Cl—C$_6$H$_4$—O—C(CH$_3$)$_2$— | —C$_6$H$_5$ | H | H | H | $n_D^{20}$ = :1.5644 |
| 5 | Cl$_2$C=CCl— | —C$_6$H$_4$—CH$_3$ | H | H | H | $^1$H-NMR: 2.34(s, 3H); 4.25(t, 1H); 7.15(s, 4H) |

-continued

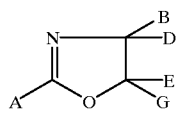
(I)

| Ex. No. | A | B | D | E | G | Physical constant |
|---|---|---|---|---|---|---|
| 6 | $Cl_2C=CCl-$ | 3-chlorophenyl | H | H | H | $^1$H-NMR: 4.23(t, 1H); 7.1–7.3(m, 4H) |
| 7 | $Cl_2C=CCl-$ | phenyl | H | H | H | $^1$H-NMR: 4.24(t, 1H); 7.2–7.4(m, 5H) |
| 8 | cyclopropyl | 4-$C_4H_9$t-phenyl | H | H | H | $n_D^{20}$ = 1.5391 |
| 9 | 2,2-dichloro-1-methyl-3-ethylcyclopropyl | 4-$C_4H_9$t-phenyl | H | H | H | m.p.: 80–85° C. |
| 10 | 2-chloro-2-fluoro-1-ethylcyclopropyl | 4-$C_4H_9$t-phenyl | H | H | H | $n_D^{20}$ = 1.5209 |
| 11 | (Cl)(Cl)C=CH-C(CH$_3$)(CH$_3$)cyclopropyl | 4-$C_4H_9$t-phenyl | H | H | H | $n_D^{20}$ = 1.5438 |
| 12 | $(FCH_2)_2C(CH_3)-$ | 4'-$OCF_3$-biphenyl-4-yl | H | H | H | m.p.: 82° C. |

Application Examples

Example A

Tetranychus test (OP resistant/dipping treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-Containing water to the desired concentrations.

Bean plants (*Phaseolus vulgaris*) which are heavily infested with all developmental stages of the red spider mite Tetranychus urticae are dipped in a preparation of the active compound of the desired concentration.

After the desired time, the destruction in % is determined. 100% means that all the spider mites have been killed; 0% means that none of the spider mites have been killed.

In this test, for example the compounds from Preparation Examples 8 and 10 brought about mortality of at least 80% after 7 days, at an exemplary concentration of active compound of 0.1%.

Example B

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the desired time, the destruction in % is determined. 100% means that all the caterpillars have been killed; 0% means that none of the caterpillars have been killed.

In this test, for example, the compound of Preparation Example 1 displays a degree of destruction of 100% after 7 days at an exemplary concentration of active compound of 0.1%.

Example C

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired time, the destruction in % is determined. 100% means that all the caterpillars have been killed; 0% means that none of the caterpillars have been killed.

In this test, for example, the compounds of Preparation Example 1 and 10 display a degree of destruction of 100% after 7 days at an exemplary concentration of active compound of 0.1%.

Example D

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (
Oryzae sativa) are treated by being dipped into the preparation of active compound of the desired concentration and are infested with larvae of the green rice leafhopper (*Nephotettix cincticeps*) while the seedlings are still moist.

After the desired time, the destruction in % is determined. 100% means that all the leafhoppers have been killed; 0% means that none of the leafhoppers have been killed.

In this test, for example, the compounds of Preparation Examples 8, 10 and 11 display a degree of destruction of at least 90% after 7 days at an exemplary concentration of active compound of 0.1%.

We claim:
1. A substituted oxazoline of the formula (I-1),

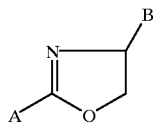

in which

A represents $C_1$–$C_6$-alkyl which is substituted one or more times by identical or different substituents selected from the group consisting of fluorine, chlorine and bromine;

represents $C_2$–$C_6$-alkenyl which is optionally substituted one or more times by identical or different substituents selected from the group consisting of fluorine, chlorine and bromine;

represents $C_3$–$C_8$-cycloalkyl which is optionally substituted one or more times by identical or different substituents selected from the group consisting of fluorine, chlorine, $C_1$–$C_4$-alkyl and $C_2$–$C_4$-alkenyl, and by $C_1$–$C_2$-alkyl or $C_2$–$C_4$-alkenyl, each of which is substituted by fluorine or chlorine;

and represents $C_5$–$C_7$-cycloalkenyl which is optionally substituted one or more times by identical or different substituents selected from the group consisting of fluorine, chlorine and $C_1$–$C_4$-alkyl and from $C_1$–$C_2$-alkyl which is substituted by fluorine and chlorine with the proviso that A is neither 2,2-dimethyl-3-buten-1-yl nor 2'(2,2dihalovinyl)3',3'-dimethylcyclopropyl; and B represents phenyl, which is optionally substituted one to four times by identical or different substituents, wherein phenyl substituents are selected from F, Cl, Br,
$C_1$–$C_{18}$-alkyl,
$C_1$–$C_6$-alkoxy-$C_1$–$C_8$-alkyl,
$C_1$–$C_8$-alkoxy which is substituted one to six times by identical or different substituents selected from the group consisting of F and Cl, $C_1$–$C_2$-alkyl which is substituted one to five times by identical or different substituents selected from the group consisting of F and Cl, $C_1$–$C_{18}$-alkoxy and —(OC$_2$H$_4$)$_{1-3}$—O—$C_1$–$C_6$-alkyl, $C_1$–$C_{12}$-alkylthio, $C_1$–$C_8$-alkylthio which is substituted one to six times by identical or different substituents selected from the group consisting of F and Cl, 3,4-difluoromethylenedioxo, 3,4-tetrafluoroethylenedioxo, the groups

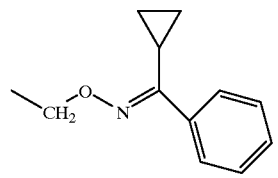

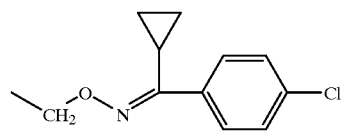

-continued

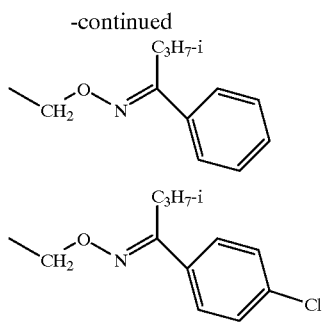

cyclohexyl and cyclohexyloxy, each of which is optionally substituted by $C_1$–$C_4$-alkyl, $C_1$–$C_4$-alkoxy, cyclohexyl or phenyl;

phenyl, benzyl, phenoxy, phenylthio, benzyloxy and benzylthio, each of which is optionally substituted one to three times by identical or different substituents selected from the group consisting of $C_1$–$C_{12}$-alkyl, F, Cl, Br, $CF_3$ and $C_1$–$C_4$-alkoxy, $C_1$–$C_4$-alkoxy, which is substituted one to six times by identical or different substituents selected from the group consisting of F and Cl, $C_1$–$C_4$-alkoxy-$C_1$–$C_4$-alkyl, $C_1$–$C_4$-alkoxyethyleneoxy, $C_1$–$C_4$-alkylthio, or $C_1$–$C_4$-alkylthio which is substituted one to six times by identical or different substituents selected from the group consisting of F and Cl.

2. A substituted oxazoline of the formula (I)

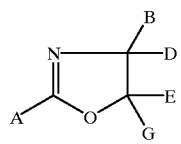

wherein
A represents

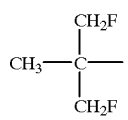

B represents

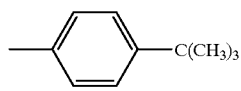

and D, E and G represent hydrogen.

3. A substituted oxazoline of the formula (I)

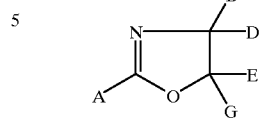

wherein
A represents

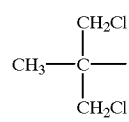

B represents

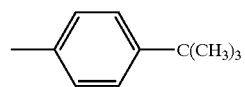

and D, E and G represent hydrogen.

4. A substituted oxazoline of the formula (I)

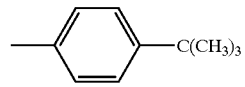

wherein
A represents

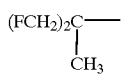

B represents

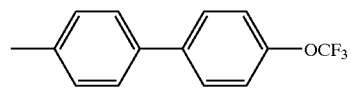

and D, E and G represent hydrogen.

5. A composition for killing arthropods and nematodes having at least one compound of the formula (I) as claimed in claim 1.

6. A method of killing arthropods and nematodes wherein an anti-arthropod and anti-nematode effective amount of a compound of the formula (I) as claimed in claim 1 is applied to arthropods and nematodes or their habitat.

* * * * *